United States Patent
Tjandrawinata et al.

(10) Patent No.: US 9,345,731 B2
(45) Date of Patent: May 24, 2016

(54) HERBAL EXTRACT AS SENSITIVITY ENHANCER TOWARD INSULIN AND ANTIDIABETES

(75) Inventors: Raymond R. Tjandrawinata, Jakarta Selatan (IN); James M. Sinambela, Bekasi (IN); Olivia Mayasari, Jakarta Utara (IN); Deasy Diah Dwi R. W., Cimahi (IN); Melissa Puspasari, Jakarta Utara (IN)

(73) Assignee: PT. DEXA MEDICA, Palembang, Sumatera Selatan (ID)

( * ) Notice: Subject to any disclaimer, the term of this patent is extended or adjusted under 35 U.S.C. 154(b) by 422 days.

(21) Appl. No.: 13/002,319

(22) PCT Filed: Aug. 4, 2009

(86) PCT No.: PCT/IB2009/053370
§ 371 (c)(1),
(2), (4) Date: Jan. 30, 2011

(87) PCT Pub. No.: WO2010/023572
PCT Pub. Date: Mar. 4, 2010

(65) Prior Publication Data
US 2011/0177177 A1 Jul. 21, 2011

(30) Foreign Application Priority Data
Aug. 27, 2008 (ID) .............................. P00200800564

(51) Int. Cl.
| A61K 36/54 | (2006.01) |
| A61K 38/00 | (2006.01) |
| A61K 38/28 | (2006.01) |
| A61P 3/10 | (2006.01) |
| A61P 7/12 | (2006.01) |
| A61K 36/185 | (2006.01) |

(52) U.S. Cl.
CPC ............... *A61K 36/185* (2013.01); *A61K 36/54* (2013.01)

(58) Field of Classification Search
None
See application file for complete search history.

(56) References Cited

U.S. PATENT DOCUMENTS

| 2005/0249827 A1* | 11/2005 | Gardiner et al. ............... 424/729 |
| 2006/0269617 A1* | 11/2006 | Giampapa ..................... 424/646 |
| 2008/0063689 A1 | 3/2008 | Farber |

FOREIGN PATENT DOCUMENTS

| WO | WO 2006108008 A2 | 10/2006 |
| WO | WO 2006127779 A2 * | 11/2006 ........... A61K 31/198 |
| WO | WO 2007056176 A2 | 5/2007 |

OTHER PUBLICATIONS

Mallavadhani et al. (2008) J. Planar Chromatography 21, 6, 461-464.*
Buhukbalci et al. (2008) Plant Foods Hum. Nutr. 63: 27-33.*
Cao et al. (2010) Phytomedicine 17, 1027-1032.*
Cao et al. (2007) Archives Biochem. Biophys. 459, 214-222.*
Cheng et al. (2012) Food Chemistry 135, 2994-3002.*
Judy et al. (2003) J. Ethnopharmacology 87, 115-117.*
Klein et al. (2007) Evid. Based Complement Alternat Med. 4(4): 401-407.*
Sheng et al. (2008) PPAR Research, Article ID 581348, 9 pages.*
Anderson et al. (2004) J. Agric. Food Chem. 52, 65-70.*
Liu et al. (2001) J. Nutr. 131: 2242-2247.*
Qin et al. (2003) Diabetes Research and Clinical Practice 62, 139-148.*
ISR in PCT/IB2009/053370.

* cited by examiner

*Primary Examiner* — Chris R Tate
*Assistant Examiner* — Russell Fiebig
(74) *Attorney, Agent, or Firm* — Neifield IP Law, PC (57) ABSTRACT

A herbal extract composition from Lythraceae and Lauraceae family plants and its usage as insulin resistance reducer, syndrome X normalization, pre-diabetes and type 2 diabetes treatments, particularly as activator in insulin signal pathway, as modulator in glucose transport system, as modulator in adiponectin secretion, and as suppressor in insulin resistance. Representative from Lythraceae family has been selected *Lagerstroemia speciosa*, and representative from Lauraceae family has been selected *Cinnamomum burmannii*. Such herbal extract composition work synergistically to strengthen pharmacological effect produced by each extract if they act alone.

2 Claims, 7 Drawing Sheets

HERBAL EXTRACT AS SENSITIVITY ENHANCER TOWARD INSULIN AND ANTIDIABETES

The present invention relates to a herbal formulation to reduce severity level of insulin resistance patient which can continue to diabetes, mainly type 2 diabetes, by increasing the balance of glucose level in the body. The herbal formulation contains *Cinnamomum burmannii* and *Lagerstroemia speciosa* extracts.

The Herbal formulation according to the present invention can be used effectively to increase glucose uptake into cell, decrease the insulin resistance level before and after diabetes development. Composition of the present invention can be used either as traditional drug or alternative therapy to syndrome X condition, insulin resistance, pre-diabetes, or diabetes patients.

BACKGROUND OF THE INVENTION

In purpose of the present invention, definition of 'natural drugs' is a pharmacological agent which gives therapeutic and curative effects from natural substances. Definition of 'pharmaceutical drugs' is a pharmacological agent which gives therapeutic and curative effects from synthetic chemical substances.

Progress and development of herb-based natural drugs are rapid thus many natural drugs are now used as alternative therapy to fight against various diseases. Millions of people in this world prefer to choose natural drugs which are derived from extract of plant and/or animal parts for many reasons, such as to reduce side effects from pharmaceutical drugs, or to get less price than pharmaceutical drugs.

According to Perkeni Center (Indonesian Endocrinology Association), Indonesia was ranked as the sixth largest diabetes population in the world after India, China, Russia, Japan, and Brazil. WHO records more than 180 millions people suffer from diabetes and this number is estimated will be doubled by 2030. In 2005, it had been recorded 1.1 millions people died because of diabetes. Diabetes Mellitus, or commonly known as sweet urine, is a disease that is characterized by excessive increase of blood glucose because the glucose can not be transported into tissues thus it is released in urine. Glucose taken in the body will be converted into energy and some of them are stored in the forms of glycogen in fat and muscle tissues. The conversion process is performed by the support of insulin secreted by pancreatic gland. Insulin regulates the balance of glucose level in the body. If the glucose level in blood is high, then there will be a biochemical change from carbohydrate into energy or glycogen storage. In diabetic patients, there is a problem in the balance regulation system of blood glucose levels.

Ninety percent diabetic are of type 2 diabetes, mainly because of insulin resistance. Insulin resistance is a condition where an insulin sensitivity decreases. Insulin sensitivity is an ability of insulin to decrease blood glucose level by suppressing hepatic glucose production and stimulating glucose usage in the muscle and adipose tissues. Cause of this insulin resistance is usually connected to the lifestyle factor such as obesity. Therefore, this type 2 diabetes treatment is expected to decrease blood sugar level and insulin resistance.

Some treatments to overcome type 2 diabetes that have been previously given were giving synthetic chemical substances such as sulphonylureas and meglinitinides (stimulating pancreas to produce more insulin), biguanides (decreasing glucose substance level produced by the liver), alpha-glucosidase inhibitors (decreasing glucose absorption from carbohydrate we eat), and thiazolidinediones (reducing insulin resistance). Among the synthetic chemical treatment toward insulin resistance, the thiazolidinedione (TZD) group, such as pioglitazone dan rosiglitazone, is the most-used insulin sensitizer. Some minerals such as chromium and vanadium have also been proposed to enhance insulin sensitivity, though they are not too potent. TZDs are substrate for PPAR-γ factor transcription thus PPAR-γ gene expression increases as the dose of TZDs given increases. However, the use of this TZD group may cause undesired adverse effects such as SGOT/SGPT level elevation (Idiosyncratic acute hepatotoxicity) and edema in patients.

*Lagerstroemia speciosa* plant from Lythraceae family has been known and used as antidiabetic drugs. Leaves of *Lagerstroemia speciosa* plant are known with the name 'bungur' in Indonesia and 'banaba' in Philippine. Japan patent No. 07-228539 taught that a fraction from *Lagerstroemia speciosa* extract could be used as active ingredient in antidiabetic agent. It also has a hypoglycemic activity. Beside that, water or alcohol extract from *Lagerstroemia speciosa* leaves and corosolic acid concentration as much as 0.01-15 mg per 100 mg concentrate are primary components in inhibiting the increase, or reducing, blood sugar levels, these are taught in US patent 2001/0006941 A1.

*Cinnamomum burmannii* plant from Lauraceae family is commonly known as cinnamon. This plant is used as food scent in making of bread dough. Some articles mention that this plant is also used as traditional drugs to overcome gastrointestinal problems such as diarrhea, vomiting, and gastroenteritis. One article mentioned that this plant could also be used as cough and flu drug, and also to treat arthritis and rheumatic.

Cinnamon (in Indonesia, *Cinnamomum burmannii*), is also believed to have a potential in either preventing or treating diabetes. Cinnamon also has a positive effect in glycemia and fat profile regulation in type 2 diabetes mellitus (WO/2008/059310, WO/2008/041049).

In the present invention, we will describe the use of *Cinnamomum burmannii* and *Lagerstroemia speciosa* extract combination as an optimal natural drug to reduce insulin resistance and also reduce blood sugar level in syndrome X, insulin resistance, pre-diabetes, or diabetes patients, mainly type 2 diabetes.

BRIEF DESCRIPTION OF THE INVENTION

The objects and/or solutions which are taught from the present invention will be set forth in the preferred embodiments. The embodiments illustrated serve the purpose of understanding the present invention, without limiting the possibilities of other embodiments which can be learned from the practice of the present invention. The objects and/or solutions which are taught in the present invention will be realized from the elements and combinations detailed in the claims herein.

To attain the solutions and in accordance with the objects of the present invention, as explained in the embodiments and broadly described in this application, the first aspect of the present invention is directed to a pharmaceutical dosage form comprises of the combination of extract(s) from (a) Lythraceae family and (b) Lauraceae family or its fraction(s) or its compound(s) which are derived therefrom, where such combination in effective dosage work synergistically to strengthen pharmacological effect produced by each single extract if they act alone. Pharmaceutical dosage forms according to the present invention also contain excipient ingredient that are pharmaceutically acceptable.

Composition of pharmaceutical dosage forms according to the present invention involves (a) extract(s) from Lythraceae family including *Lagerstroemia speciosa* derived from water extraction process and/or other polar solvents, and (b) extract(s) from Lauraceae family including *Cinnamomum burmannii* derived from water extraction process and/or other polar solvents.

The second aspect of the present invention is directed to the combination usage of Lythraceae and Lauraceae family plant extracts to enhance insulin sensitivity via stimulation of intracellular signaling pathway of PI3 kinase, Akt, PPAR-γ, PPAR-δ, and Glut-4 genes.

The third aspect of the present invention is directed to the combination usage of Lythraceae and Lauraceae family plant extracts to modulate Adiponectin secretion.

The fourth aspect of the present invention is directed to the combination usage of Lythraceae and Lauraceae family plant extracts to enhance insulin sensitivity via inhibition of Resistin gene intracellular signaling pathway.

The fifth aspect of the present invention is directed to the combination usage of Lythraceae and Lauraceae family plant extracts to enhance glucose uptake into cell via stimulation Glut-4 gene intracellular signaling pathway.

The sixth aspect of the present invention is directed to toxicity test of the combination usage of Lythraceae and Lauraceae family plant extracts towards cell viability.

BRIEF DESCRIPTION OF THE DRAWINGS

The accompanying drawings, which are incorporated in and constitute a part of the specification of the present application, illustrate one or several embodiments of the invention. These drawings serve to explain the principles which are taught by the present invention.

DETAILED DESCRIPTION OF THE INVENTION

The present invention will be made in detail by ways of examples without limiting the scope of the invention to the examples provided.

The present invention teaches the combination of Lythraceae family plant extract, such as the *Lagerstroemia speciosa*, and Lauraceae family plant extract, such as for example *Cinnamomum burmannii*, that have been previously known as antidiabetic drugs. Each extract of Lythraceae and Lauraceae family plant has different pharmacological effects. But if they are combined, both extracts will interact themselves that cause the native characteristic of each extract works synergistically to strengthen the pharmacological activity with special treatment modality in clinical trial.

The present invention teaches that *Lagerstroemia speciosa* as a representative from Lythraceae herb family consists of a compound that is able to control hypoglycemic activity and activates glucose transport. While *Cinnamomum burmannii* is selected as a representative from Lauraceae herb family because the compounds in this herb form secondary metabolites and are estimated to have an activity as a modulator in insulin signaling pathway.

*Lagerstroemia speciosa* contains corosolic acid. *Lagerstroemia speciosa* extract also contains alkaloid, astragalin, brevifolin, carboxylic acid, corilagin, cymene, ellagic acid, ellagitannin, gallocatechin, geraniin, hypophyllantin, lignan, lintetralin, lupeol, methyl salicylate, niranthin, nirtetralin, niruretin, nirurin, niruriside, norsecurinine, phyllanthin, phyllanthenol, phyllochrysine, phyltetralin, repandusinic acids, quercetin, quercetol, quercitrin, rutin, saponin, triacontanal, tricontanol, and/or its combinations.

*Cinnamomum burmannii* contains polyphenol, or tannin compounds, terpenoid, sterol, aldehid, resin, including ellagitannin, gallotannin, galloyl group, glucoside, glucokinin, ethyl cinnamate, eugenol, cinnamaldehyde, beta-carophyllene, linalool, methyl chavicol, and/or its combinations. *Cinnamomum burmannii* extract also contains thymoquinone, dithymoquinone, nigellone, thymohydroquinone, thymol, alkaloid diterpene type dolabellane, nigellamines A(1)(1), A(2)(2), B(1)(3), and B(2)(4), and/or its combinations.

A. Extraction Process of *Lagerstroemia Speciosa* and *Cinnamomum Burmannii*

Extraction process was initialized with raw material maceration in a polar solvent for example water until completely macerated and micelles were produced; heated in extractor. The raw materials that had been diced, were weighed and stirred until homogeneous. The homogeneous raw materials then were added into extractor containing Warm/heated water. The mixed raw materials were macerated for 1 hour. Micelles were withdrawn by filtration process. Micelles then were evaporated by vacuum until they were concentrated. The concentrate was then dried using vacuum oven. The Extract was then weighed and grounded until it became fine powder. Later, it was filtered using a sieve with appropriate mesh. The result was weighed and recorded.

As an alternative, extraction process according to this present invention can also be performed using other polar solvents in various concentrations as needed. For example, the ethanol or methanol solvent. According to the following study, combination of *Lagerstroemia speciosa* plant extract as a representative from Lythraceae herb family and *Cinnamomum burmannii* plant extract which was selected as a representative from Lauraceae herb family in a certain dose showed an activity as activator in insulin signaling pathway.

B. *Lagerstroemia Speciosa* and *Cinnamomum Burmannii* Effects as Activator in Insulin Signaling Pathway METHODS: 3T3 Swiss Albino cells were purchased from European Collection of Cell Culture (Salisbury, UK). Cells were cultured using specific supplemented medium.

3T3 Swiss Albino cells were cultured in 10 cm-diameter plates. Treatments were given by administering the combination of *Lagerstroemia speciosa* and *Cinnamomum burmannii* extract in a range of dose 1-10 μg/ml, pioglitazone and glimepiride (as control) to observe the expression of some target genes. The combination extract stock was dissolved in water solvent containing 5% ethanol. *Lagerstroemia speciosa* extract contains corosolic acid, while *Cinnamomum burmannii* extract contains polyphenol. Pioglitazone stock was made in concentration of 10 mM in DMSO 1% solvent, while Glimepiride stock was made in concentration of 10 mM in dichloromethane solvent. Treatments were administered in 24 and 48 hours incubation time. RNAs from 3T3 Swiss Albino cells were extracted using Trizol reagent (Invitrogen, Carlsbad, USA), RNAs then were reverse transcribed into cDNA and amplified by PCR using specific primers. PCR products were analyzed by electrophoresis using ethidium bromide.

Figure 1:
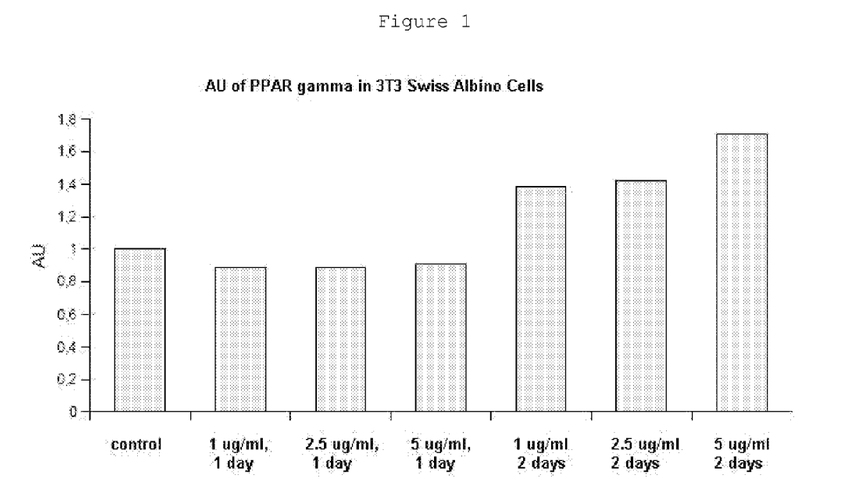
FIG. 1 is the graphic of PPAR-γ expression in mRNA level with combination of Lythraceae and Lauraceae family plant extracts administration in 3T3 Swiss Albino cells.

RESULTS: FIG. 1 illustrates that the treatment with the extract combination in a dose range 1-5 μg/ml for 24 hours incubation did not give any effect in PPAR-γ gene expression in 3T3 Swiss Albino cells. While in the treatment with the 5 μg/ml combination extract for 48 hours incubation increased the gene expression of PPAR-γ in 3T3 Swiss Albino cells.

Figure 2:
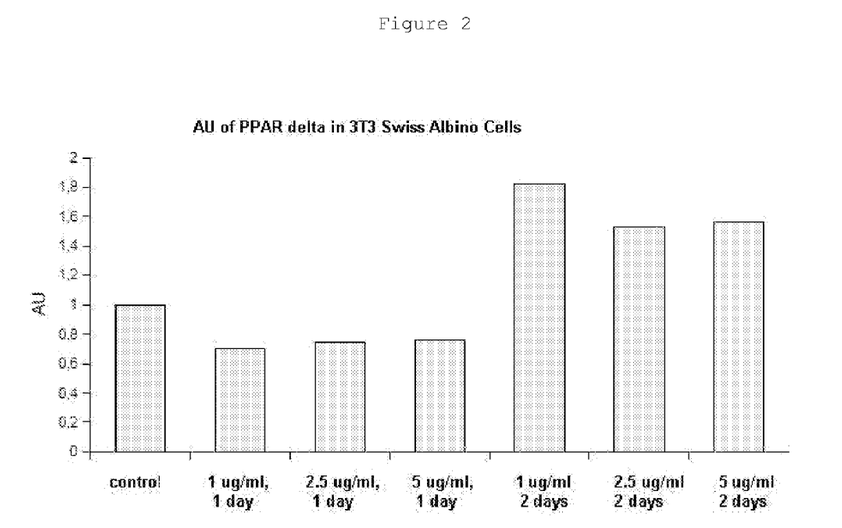
FIG. 2 is the graphic of PPAR-δ expression in mRNA level with combination of Lythraceae and Lauraceae family plant extracts administration in 3T3 Swiss Albino cells.

FIG. 2 illustrates that the treatment with the extract combination in a dose range 1-5 μg/ml for 24 hours incubation did not give any effect in PPAR-δ gene expression in 3T3 Swiss Albino cells. While in the treatment with the 1 μg/ml combination extract for 48 hours incubation increased the gene expression of PPAR-δ in 3T3 Swiss Albino cells.

Figure 3:
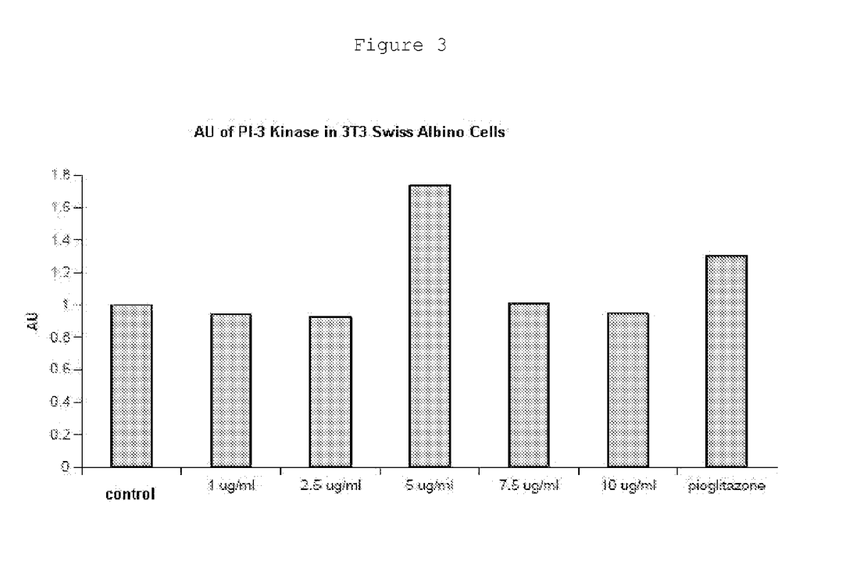
FIG. 3 is the graphic of PI3 kinase expression in mRNA level with combination of Lythraceae and Lauraceae family plant extracts in 3T3 Swiss Albino cells.

FIG. 3 illustrates that the treatment with the 5 μg/ml extract combination for 48 hours incubation increased the gene expression of PI-3 Kinase in 3T3 Swiss Albino cells.

Figure 4:
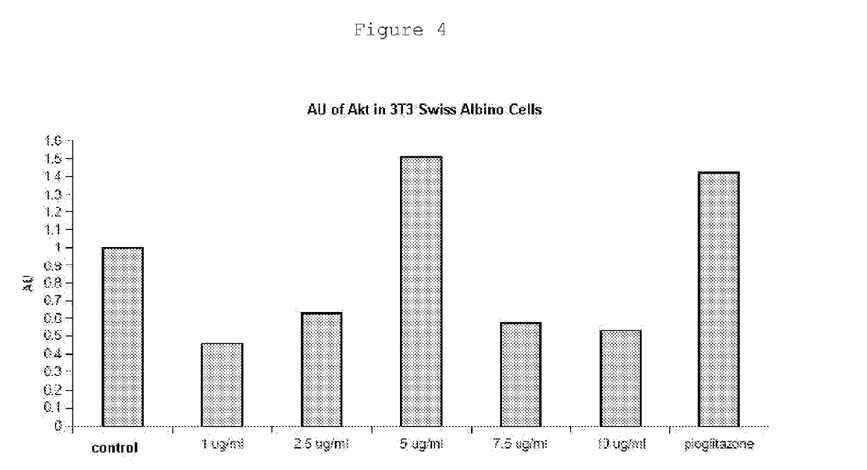
FIG. 4 is the graphic of Akt expression in mRNA level with combination of Lythraceae and Lauraceae family plant extracts administration in 3T3 Swiss Albino cells.

FIG. 4 illustrates that the treatment with the 5 μg/ml extract combination for 48 hours incubation increased the gene expression of Akt in 3T3 Swiss Albino cells.

Figure 5:
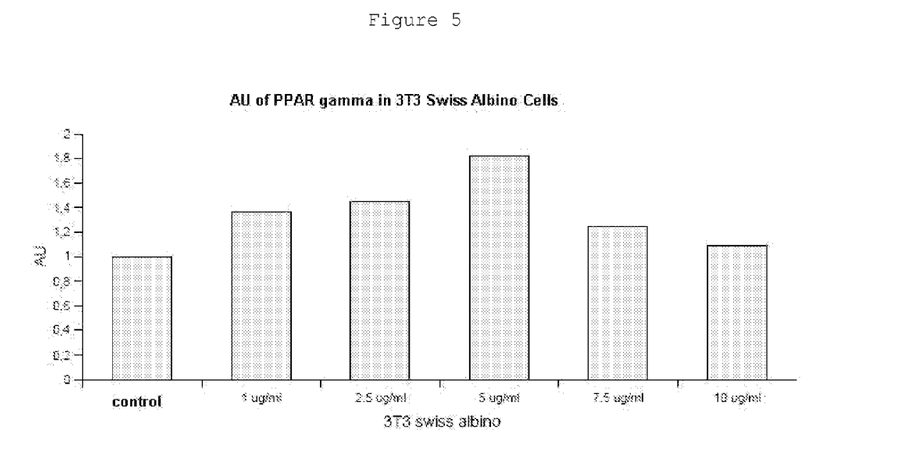
FIG. 5 is the graphic of PPAR-γ expression in mRNA level with combination of Lythraceae and Lauraceae family plant extracts administration in 3T3 Swiss Albino cells.

FIG. 5 illustrates that the treatment with the 5 μg/ml extract combination for 48 hours incubation increased the gene expression of PPAR-γ in 3T3 Swiss Albino cells.

Figure 6:
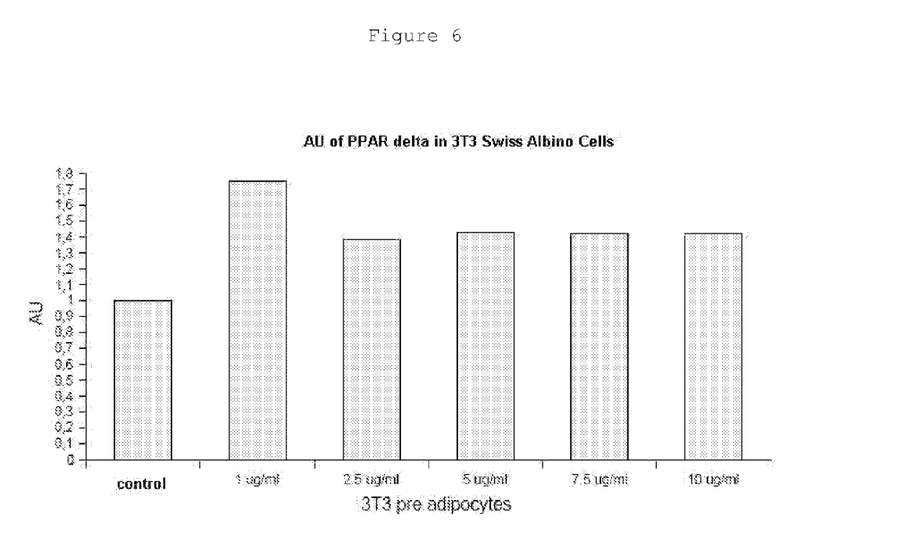
FIG. 6 is the graphic of PPAR-δ expression in mRNA level with combination of Lythraceae and Lauraceae family plant extracts administration in 3T3 Swiss Albino cells.

FIG. 6 illustrates that the treatment with the 1 μg/ml extract combination for 48 hours incubation increased the gene expression of PPAR-δ in 3T3 Swiss Albino cells.

The graphics in FIGS. 1-6 showed that the extract combination was able to increase gene expressions involved in insulin activation pathway, namely PI-3 Kinase, Akt, PPAR-γ and PPAR-δ genes. Administration of extract combination of *Lagerstroemia speciosa* and *Cinnamomum burmannii* with the concentrate of 5 μg/ml for 48 hours was able to increase some transcription factor expressions that enhance insulin sensitivity; they are PI-3 Kinase, Akt, dan PPAR-γ genes in 3T3 Swiss Albino cells. Administration of extract combination of *Lagerstroemia speciosa* and *Cinnamomum burmannii* with the concentrate of 1 μg/ml for 48 hours was able to increase PPAR-δ gene expression in 3T3 Swiss Albino cells.

The present invention teaches the use of the combination of Lythraceae and Lauraceae family plant extracts as a modulator in glucose transport system to enhance glucose uptake into cell. For the purpose of the experiment, combination of *Lagerstroemia speciosa* extract as a representative from Lythraceae herb family and *Cinnamomum burmannii* extract as a representative from Lauraceae herb family were prepared. The following study was done to observe the extract combination as a modulator in glucose transport.

C. Combination of *Lagerstroemia Speciosa* and *Cinnamomum Burmannii*

Extracts as Modulator in Glucose Transport System

METHODS: 3T3 Swiss Albino cells were purchased from European Collection of Cell Culture (Salisbury, UK). Cells were cultured using specific supplemented medium.

3T3 Swiss Albino cells were differentiated until 3T3 Swiss Albino pre-adipocytes and 3T3 Swiss Albino adipocytes cells were obtained. Each cell type received excessive glucose for over 2 weeks. Incubated cells received such excessive glucose were used as insulin resistance model. After that, those four type cells obtained were tested for its ability to uptake glucose in media. The remaining glucose level was analyzed so that the glucose level uptaken by each 3T3 Swiss Albino cell type could be determined.

3T3 Swiss Albino cells were cultured in 10 cm-diameter plates. Treatments were given by administering the extract combination of *Lagerstroemia speciosa* and *Cinnamomum burmannii* extracts in a dose range of 1-10 μg/ml, pioglitazone and glimepiride (as control) to observe the expression of some target genes. The extract combination stock was dissolved in water solvent contained 5% ethanol. *Lagerstroemia speciosa* extract contains corosolic acid, while *Cinnamomum burmannii* extract contains polyphenol. Pioglitazone stock was made in concentration of 10 mM in 1% DMSO solvent while Glimepiride stock was made in concentration of 10 mM in dichloromethane solvent. Treatments were administered in 24 hours and 48 hours time of incubation. RNAs from 3T3 Swiss Albino cells were extracted using Trizol reagent (Invitrogen, Carlsbad, USA), the RNAs then were reverse transcribed into cDNAs and amplified by PCR using specific primers. The PCR products were analyzed by electrophoresis using ethidium bromide.

To measure glucose level that was uptaken by cell, we used an experiment method which is initialized by culturing 3T3 Swiss Albino cells in 6 cm-diameter plates. After the cells reached 80% confluency in plates, the cells were washed with PBS then added 10 mg/ml glucose solution with and/or without addition of the extract combination of *Lagerstroemia speciosa* and *Cinnamomum burmannii* extracts, then the cells were incubated for 48 hours. Glucose concentration that was uptaken by cells was measured by subtracting the initial glucose concentration with the remaining glucose in media at the end of incubation time. The sample to be measured was added into a reaction tube and was reacted with anthrone reagent. The reaction result was quantified by spectrophotometer.

Figure 7:
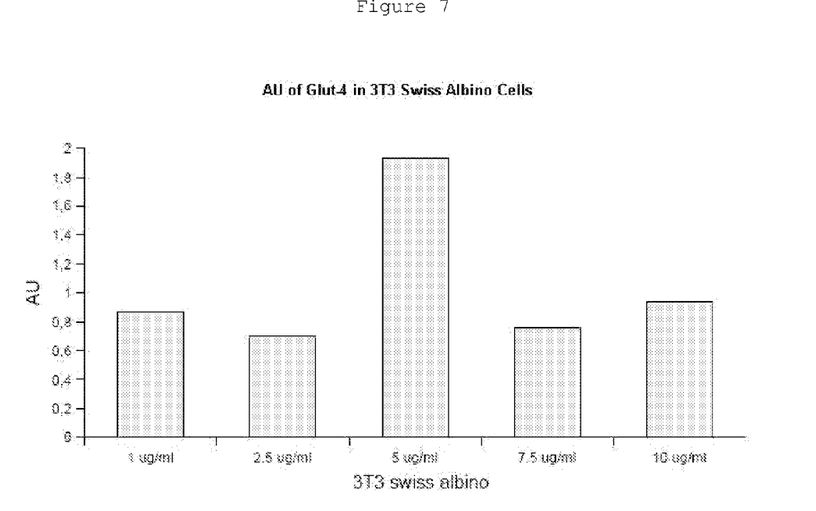
FIG. 7 is the graphic of Glut-4 expression in mRNA level with combination of Lythraceae and Lauraceae family plant extracts administration in 3T3 Swiss Albino cells.

RESULTS: FIG. 7 illustrates that treatment with the 5 μg/ml extract combination of *Lagerstroemia speciosa* and *Cinnamomum burmannii* extracts, for 48 hours increased Glut-4 gene expression in 3T3Swiss Albino cells.

Figure 8:
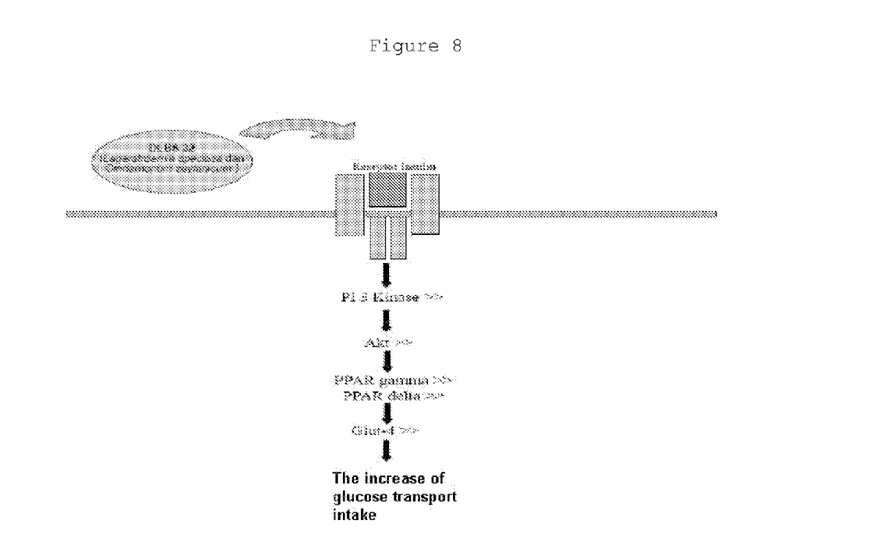
FIG. 8 shows estimated illustration of mechanism of action pathway of Lythraceae and Lauraceae family plant combination extracts administration in enhancing glucose uptake into 3T3 Swiss Albino cells.

FIG. 8 illustrates the mechanism of action estimated from the extract combination of *Lagerstroemia speciosa* and *Cinnamomum burmannii*, in enhancing glucose transport into cells. The extract combination was able to increase insulin sensitivity to recognize its receptor; so there would be an intracellular activation such as signal transduction stimulation initialized by the increase of phosphorylated PI3 Kinase expression, thus resulting in the increase of Akt followed by several other transcriptions factors such as PPAR-γ and PPAR-δ. Those increasing genes also increased Glut-4 gene expression so that the glucose transporter protein was activated and therefore increased the glucose transport into cells.

Figure 11:
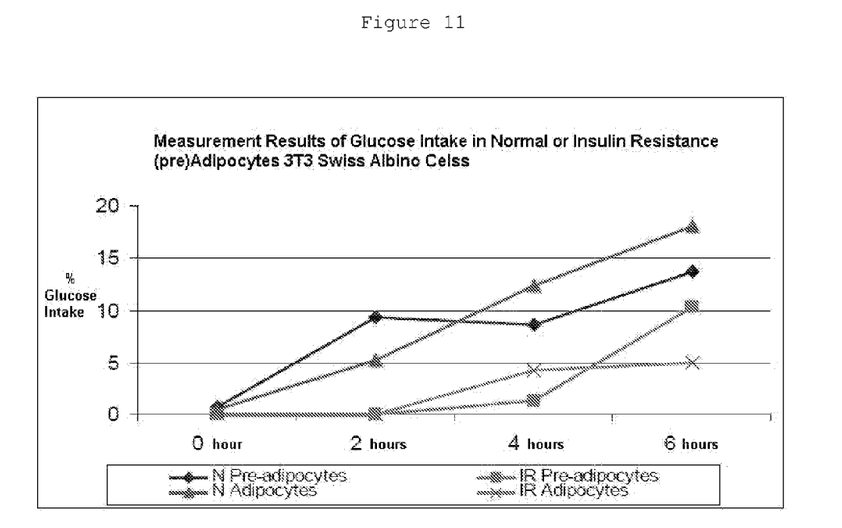
FIG. 11 is the graphic of glucose measurement results obtained from normal pre-adipocytes 3T3 Swiss Albino cells, insulin resistance pre-adipocytes 3T3 Swiss Albino, normal adipocytes 3T3 Swiss Albino, and insulin resistance adipocytes 3T3 Swiss Albino after incubation with 5 mg/ml glucose for 0, 2, 4, 6 hours.

FIG. 11 illustrates that the glucose level uptaken by normal adipocytes 3T3 Swiss Albino was much more than normal pre-adipocytes 3T3 Swiss Albino cells. The glucose level uptaken by insulin resistance adipocytes 3T3 Swiss Albino cells in fact was much more than insulin resistance pre-adipocytes 3T3 Swiss Albino cells. The glucose level uptaken by either insulin resistance pre-adipocytes or adipocytes 3T3 Swiss Albino cells in fact was far less than either normal pre-adipocytes or adipocytes 3T3 Swiss Albino cells.

Figure 12:
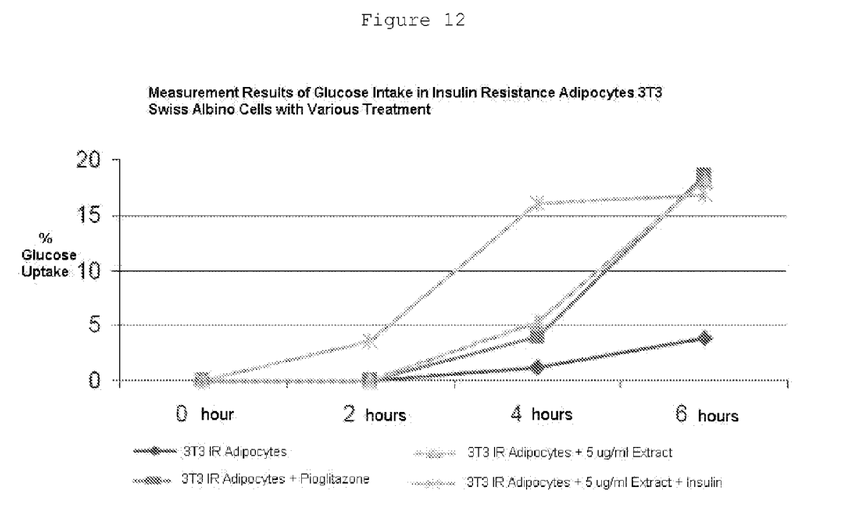
FIG. 12 is the graphic of glucose measurement results obtained from insulin resistance adipocytes 3T3 Swiss Albino after administration of 5 μg/ml Lythraceae and Lauraceae family plant combination extracts or 0.02 μM pioglitazone and/or 25 nM insulin during 48 hours incubation, then incubation with 5 mg/ml glucose for 0, 2, 4, 6 hours.

FIG. 12 illustrates the glucose level uptaken by insulin resistance adipocytes 3T3 Swiss Albino cells was only less than 5%. The extract combination administration in insulin resistance adipocytes 3T3 Swiss Albino cells was able to uptake much more glucose than before the cells were treated. Pioglitazone administration in insulin resistance adipocytes 3T3 Swiss Albino cells was also able to uptake much more glucose than control. Glucose level enhancement uptaken by insulin resistance adipocytes 3T3 Swiss Albino cells that was treated with the extract combination or pioglitazone, showed a significant result from the initial 5% became 20%.

The present invention proves the use of the extract combination of *Lagerstroemia speciosa* and *Cinnamomum burmannii* was able to enhance glucose transport into 3T3 Swiss Albino cells. Glut-4 is a membrane protein as path of glucose intake into cell, therefore the increase of Glut-4 expression shows an increase of glucose concentration uptaken by cells.

The following study teaches about the use of the extract combination of Lythraceae and Lauraceae plant families as modulator in Adiponectin secretion. For the purpose of the experiment, it has been prepared an extract combination of *Lagerstroemia speciosa* as a representative from Lythraceae herb family and *Cinnamomum burmannii* as a representative from Lauraceae herb family. The following experiment was done to observe the extract combination of *Lagerstroemia speciosa* and *Cinnamomum burmannii* as modulator in Adiponectin secretion.

D. The Extract Combination of *Lagerstroemia Speciosa* and *Cinnamomum Burmannii* as Modulator in Adiponectin Secretion METHODS: 3T3 Swiss Albino cells were purchased from European Collection of Cell Culture (Salisbury, UK). The cells were cultured using specific supplemented medium.

The 3T3 Swiss Albino cells were cultured in 10-cm diameter plates. Treatments were administered by adding the extract combination of *Lagerstroemia speciosa* and *Cinnamomum burmannii* in various dose of 1-10 μg/ml, pioglitazone and glimepiride (as control) to observe the expression of some target genes. The extract combination stock was dissolved in water solvent contained 5% ethanol. *Lagerstroemia speciosa* extract contains corosolic acid, while *Cinnamomum burmannii* extract contains polyphenol. Pioglitazone stock was made in concentration of 10 mM dissolved in 1% DMSO, while Glimepiride stock was made in concentration of 10 mM dissolved in dichloromethane. Treatments were administered in 24 and 48 hours time incubation. RNAs from 3T3 Swiss Albino cells were extracted using Trizol reagent (Invitrogen, Carlsbad, USA), the RNAs were then reverse transcribed into cDNAs and amplified by PCR using specific oligonucleotide primers. The PCR products were analyzed by electrophoresis using ethidium bromide.

Figure 9:
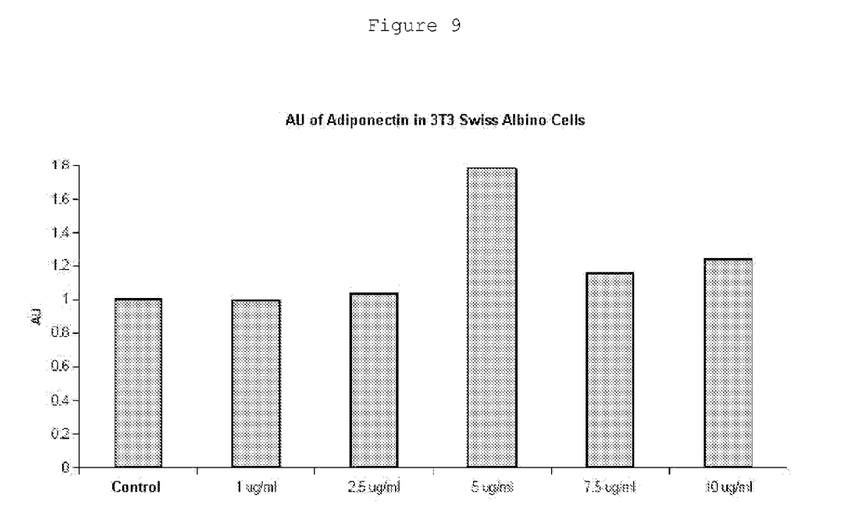
FIG. 9 is the graphic of Adiponectin expression in mRNA level with combination of Lythraceae and Lauraceae family plant extracts administration in 3T3 Swiss Albino cells.

RESULTS: FIG. 9 illustrates that the treatment with the 5 μg/ml extract combination of *Lagerstroemia speciosa* and *Cinnamomum burmannii* extracts for 48 hours was able to increase the gene expression of Adiponectin in 3T3 Swiss Albino cells.

This experiment also proves the use of the extract combination might be a transcription factor that increases the insulin sensitivity and modulates adipocytokine secretion. Adiponectin is a protein secreted by adipose tissue. The more obese a person is, the lower adiponectin level in his/her body, meaning insulin resistance will increase. Adiponectin is known to accelerate glucose metabolism thus if the adiponectin level is high, then the insulin job quality will increase, and therefore the insulin sensitivity will also increase as a result.

The present invention teaches about the use of the extract combination of Lythraceae and Lauraceae plant families as an insulin resistance lowering agent.

E. The Extract Combination of *Lagerstroemia Speciosa* and *Cinnamomum Burmannii* as an Insulin Resistance Lowering Agent METHODS: 3T3 Swiss Albino cells were purchased from European Collection of Cell Culture (Salisbury, UK). The cells were cultured in specific supplemented medium.

The 3T3 Swiss Albino cells were cultured in 10-cm diameter plates. Treatments were administered by adding the extract combination of *Lagerstroemia speciosa* and *Cinnamomum burmannii* in various dose of 1-10 μg/ml, pioglitazone and glimepiride (as control) to observe the expression of some target genes. The extract combination stock was dissolved in water solvent contained 5% ethanol. *Lagerstroemia speciosa* contains corosolic acid, while *Cinnamomum burmannii* extract contains polyphenol. Pioglitazone stock was made in concentration of 10 mM dissolved in 1% DMSO, while Glimepiride stock was made in concentration of 10 mM dissolved in dichloromethane. Treatments were administered in 24 and 48 hours time incubation. RNAs from 3T3 Swiss Albino cells were extracted using Trizol reagent (Invitrogen, Carlsbad, USA), the RNAs were then reverse transcribed into cDNAs and amplified by PCR using specific oligonucleotide primers. The PCR products were analyzed by agarose electrophoresis using ethidium bromide.

Figure 10:
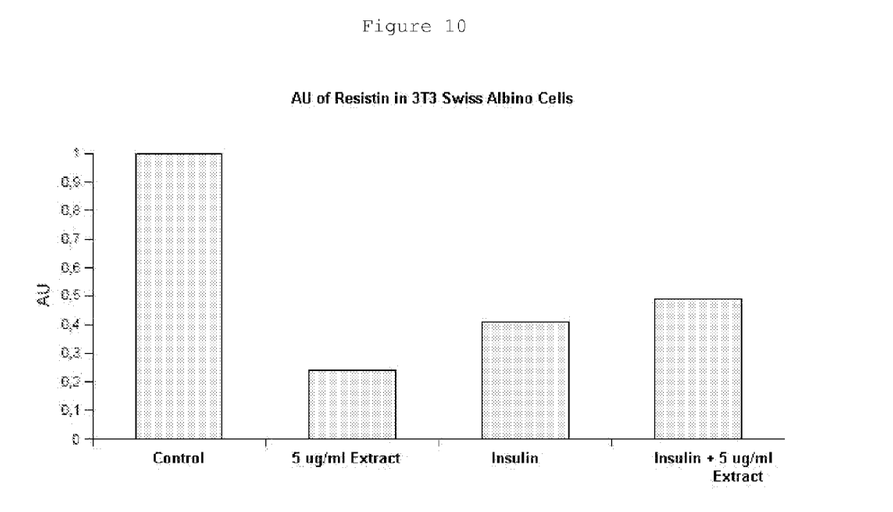
FIG. 10 is the graphic of Resistin expression in mRNA level with combination of Lythraceae and Lauraceae family plant extracts administration with or without insulin in 3T3 Swiss Albino cells.

RESULTS: FIG. 10 illustrates that the treatment with the 5 μg/ml extract combination for 48 hours was able to lower Resistin gene expression in 3T3 Swiss Albino cells. Resistin is a protein secreted by adipose tissue as result of insulin resistance enhancement. Resistin gene expression was proportional with insulin resistance, it means that if the resistin gene expression decreases, then insulin resistance will also decrease. This experiment also strengthen the proof of the extract combination use to increase insulin sensitivity or in other word is able to lower insulin resistance.

F. In Vitro Toxicity Test of the Extract Combination of *Lagerstroemia Speciosa* and *Cinnamomum Burmannii*

METHODS: 3T3 Swiss Albino cells were cultured in 96-well plates. The cells were then administered with the extract combination of *Lagerstroemia speciosa* and *Cinnamomum burmannii* in a range of dose 1-10 µg/ml, pioglitazone and glimepiride (as control) for 48 hours to study the extract toxicity towards cells. Each well was added MTT reagent and the number of living cells was counted using a spectrometer.

Figure 13:
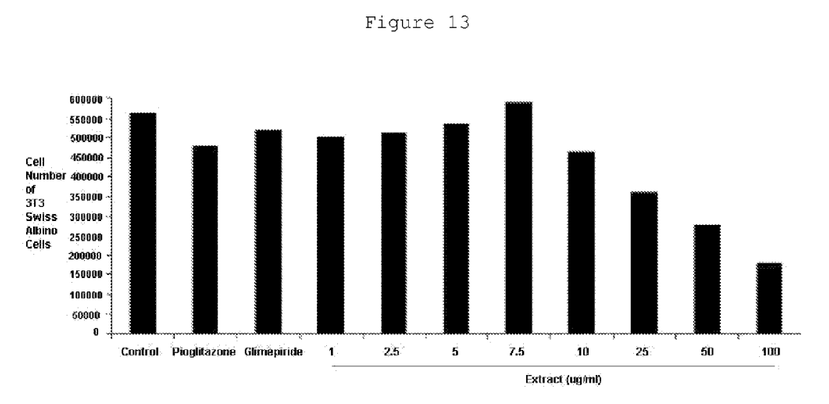
FIG. 13 is the graphic of dose variation effects from Lythraceae and Lauraceae family plant extracts combination toward 3T3 Swiss Albino cell viability during 48 hours incubation.

RESULTS: FIG. 13 illustrates that addition of extract combination of *Lagerstroemia speciosa* and *Cinnamomum burmannii* up to 7.5 µg/ml did not affect cell viability significantly compared to control. Dose addition more than 7.5 µg/ml made 3T3 Swiss Albino cells decreased significantly thus more than 50% cells were death. Addition of pioglitazone and glimepiride 0.02 µM did not show any effect toward 3T3 Swiss Albino cell viability. This result showed that the extract combination of *Lagerstroemia speciosa* and *Cinnamomum burmannii* in dose range under 7.5 µg/ml did not affect proliferation of 3T3 Swiss Albino cells as a whole.

G. Pharmaceutical Dosage Forms and Nutraceutical

This invention also includes pharmaceutical compositions and dosage forms contained *Lagerstroemia speciosa* and *Cinnamomum burmannii* extracts in an amount that is effective as an active ingredient in mixed herbs dosage form, including carrying agents, excipients or additive substances that pharmaceutically acceptable and physiologically suitable.

In the process of making pharmaceutical composition according to this invention, active ingredients of *Lagerstroemia speciosa* and *Cinnamomum burmannii* extracts mixed with excipient(s), dissolved by excipient(s) or mixed in carrying agent(s) that can be made in form of capsule, sachet, paper, also other materials or other packaging. If pharmaceutically approved excipient is used as a solvent, the excipient can be in form of solid, semi-solid or liquid (oral and injection), that reacts as a carrier or medium for the active substance. Thus, pharmaceutical composition according to this invention can be made in form of pill, capsule, tablet, powder, sachet, solution, syrup, emulsion, suspension, effervescence tablets, gel, ointment, cream, and mouthwash, massage oil, suppository, or injection.

Beside that, pharmaceutical composition contains *Lagerstroemia speciosa* and *Cinnamomum burmannii* extracts according to this invention can also be made as supplement, vitamin, jamu, herbal mix, also food and beverage production. In food production, herbal combination can be made in form of biscuit, bread or cake. In beverage production, such herbal combination can be made in form of juice, jelly, etc.

Some examples of suitable excipients are microcrystalline cellulose, gelatin, lactose, dextrose, sucrose, sorbitol, mannitol, flour, calcium phosphate, calcium silicate, etc. Formulation according to this invention may also contain lubrication agents (such as talc, stearic magnesium, mineral oil), wetting agent, preservative agent, sweetener and flavoring.

Composition according to this invention can also be made with formulation that cause active ingredients to release either directly, sustained, or controlled after the patient received such composition using methods that have been applied in pharmaceutical industry. Tablet or pill according to this invention can be layered to extend the half life of the extract thus its frequency of administration can be reduced.

Method of formulating this extract in a solid form, such as tablet, can be done through mixing of the active ingredients, *Lagerstroemia speciosa* and *Cinnamomum burmannii* extract, with excipient(s) to form an initial formulation contained homogeneous mix from the composition according to this invention. The initial formulation is a mix contained the active ingredients of the *Lagerstroemia speciosa* and *Cinnamomum burmannii* extract dispersed homogeneously so it can be properly distributed into the required dose in a dosage form, for example capsule, tablet, or pill.

Tablet or pill according to this invention can be added with a protection layer to reduce or cover bitter from the composition or active substances of *Lagerstroemia speciosa* and *Cinnamomum burmannii* extract.

*Lagerstroemia speciosa* and *Cinnamomum burmannii* extracts in effective amount or dose according to this invention is the amount or dose which the *Lagerstroemia speciosa* and *Cinnamomum burmannii* extracts is able to increase insulin sensitivity and antidiabetes. The effective amount depends on the physical condition of the patient, including weight, age, etc. According to this invention, the preferred amount or single dose or formulation of *Lagerstroemia speciosa* and *Cinnamomum burmannii* extracts mix is about 25-250 mg for 2-4 times a day as needed and indicated.

*Lagerstroemia speciosa* and *Cinnamomum burmannii* extracts according to this invention can be used effectively to increase glucose transport into cells, also to lower insulin resistance level before and after diabetes development.

*Lagerstroemia speciosa* and *Cinnamomum burmannii* extracts composition according to the present invention can be used as conventional drug or alternative therapy for syndrome X, insulin resistance, pre-diabetic also diabetic patients.

For example, one of solid dosage forms from the herbal formulation according to the present invention is gelatin capsule which contains active ingredient components of *Lagerstroemia speciosa* and *Cinnamomum burmannii* extracts; it is combined with additional substance such as inert filler, lubricant, adsorbent, or disintegrating agent. Some examples of inert filler that can be used such as Microcrystalline cellulose, Avicell, lactose, cornstarch, dicalcium phosphate, and/or other similar agents.

In formulating the tablet, active ingredient component(s) of *Lagerstroemia speciosa* and *Cinnamomum burmannii* extract can be combined with inert filler agent such as in capsule formulation; binding agent such as corn starch, Polyvinilpyrolidone, gelatin, and/or other similar agent; disintegrating agent such as cornstarch, potato starch, alginate acid, and/or other similar agent; and lubricant such as stearic acid or stearic magnesium, and/or other similar agent. Such agents then are prepared to make tablet (tableting).

To make tablet and capsule dosage forms, sweetener can also be used such as sucrose, lactose, saccharin, and/or other similar agents. In general, such tablet can also be layered with polymer, sugar solution, or its combinations.

Other examples, in formulating effervescence tablet in herbal formulation, besides using the above components in formulating tablet and capsule, certain components which produce a desired effervescence effect is also needed. Usage of acid compound combinations (such as citric acid, malic acid, tartaric acid, and or other similar agent, either in single or combination form) and base compound (such as sodium bicarbonate, sodium carbonate, and/or other similar agent) in optimum amount in a formula will produce a good effervescence effect.

In liquid dosage form, such as beverage from herbal formulation, can be formulated by mixing active ingredient component(s) of *Lagerstroemia speciosa* and *Cinnamomum burmannii* extracts with water and surfactant such as hydroxypropyl-cellulose and/or other similar agent.

In formulating herbal syrup, agents that were stated in the above beverage production are also needed. In addition, other components are also needed such as viscosity agent, stabilizing agent, etc.

In formulating semi solid dosage form such as jelly, the active ingredient component(s) of *Lagerstroemia speciosa* and *Cinnamomum burmannii* extracts can be mixed with certain hydrocoloid such as gelatin, carrageenan, pectin, arabic gum, guar gum, and/or other similar agent.

Herbal formulation in solid food, such as biscuit, bread, and cake, can be formulated by using the active ingredient component(s) of *Lagerstroemia speciosa* and *Cinnamomum burmannii* extracts as component(s) with important effect for health. Formulating solid food such as biscuit, bread, and cake according to the present invention can be done as general by using materials such as butter, sugar, egg, salt, and other supporting materials.

H. Application in Industry

Pharmaceutical dosage forms from the *Lagerstroemia speciosa* and *Cinnamomum burmannii* extracts can be produced in industrial scale of extract production, dry powder extract, and or other pharmaceutical dosage forms particularly oral either solid, semi solid, or liquid in its usage as sensitivity enhancer toward insulin and antidiabetes.

REFERENCES

Klein, G., Kim, J., Himmeldirk, K., Cao, Y., Chen, X. 2007. Antidiabetes and anti-obesity activity of *Lagerstroemia speciosa*. Evid Based Complement Alternat Med. 2007, 4(4): 401-407.

Ragasa, C. Y., Ngo, H. T., Rideout, J. A. 2005. Terpenoids and sterols from *Lagerstroemia speciosa*. J. Asian Nat Prod Res. 2005, 7(1):7-12.

The invention claimed is:

1. A food or pharmaceutical composition for treating diabetes consisting essentially of a powdered micelle product obtained from *Lagerstroemia speciosa* (*L. speciosa*) and *Cinnamomum burmannii* (*C. burmannii*), wherein the powdered micelle product is produced by a method comprising the steps of:
   (a) mixing together dried plants of *C. burmannii* and *L. speciosa* in a ratio of 3:1;
   (b) macerating the mixture with water at a temperature of between 50° C. and 90° C. for at least one hour to form micelles;
   (c) filtering the macerated mixture to collect the micelles;
   (d) concentrating the micelles by vacuum evaporation;
   (e) drying the concentrated micelles in an oven to produce dried micelles, and
   (f) grinding the dried micelles to form the powdered micelle product.

2. A method of treating diabetes in a human in need thereof, comprising administering to the human an effective amount of the food or pharmaceutical composition according to claim 1.

* * * * *